US011830589B2

(12) United States Patent
Chen et al.

(10) Patent No.: US 11,830,589 B2
(45) Date of Patent: Nov. 28, 2023

(54) DISEASE CLASSIFICATION METHOD AND DISEASE CLASSIFICATION DEVICE

(71) Applicants: Acer Incorporated, New Taipei (TW); Acer Medical Inc., New Taipei (TW); Taipei Veterans General Hospital, Taipei (TW)

(72) Inventors: Jun-Hong Chen, New Taipei (TW); Tsung-Hsien Tsai, New Taipei (TW); Chun-Hsien Li, New Taipei (TW); Wei-Ting Wang, Taipei (TW); Yin-Hao Lee, Taipei (TW); Hao-Min Cheng, Taipei (TW)

(73) Assignees: Acer Incorporated, New Taipei (TW); Acer Medical Inc., New Taipei (TW); Taipei Veterans General Hospital, Taipei (TW)

( * ) Notice: Subject to any disclaimer, the term of this patent is extended or adjusted under 35 U.S.C. 154(b) by 199 days.

(21) Appl. No.: 17/084,587

(22) Filed: Oct. 29, 2020

(65) Prior Publication Data
US 2022/0084635 A1   Mar. 17, 2022

(30) Foreign Application Priority Data
Sep. 15, 2020 (TW) ................... 109131748

(51) Int. Cl.
*G16H 10/40* (2018.01)
*G16H 50/30* (2018.01)
*G06N 7/01* (2023.01)

(52) U.S. Cl.
CPC ............... *G16H 10/40* (2018.01); *G06N 7/01* (2023.01); *G16H 50/30* (2018.01)

(58) Field of Classification Search
CPC ......... G16H 10/40; G16H 50/30; G06N 7/005
See application file for complete search history.

(56) References Cited

U.S. PATENT DOCUMENTS 8,636,660 B1    1/2014  Cohn
8,712,696 B2 *  4/2014  Eguiara ................... A61P 37/06
                                                  707/700
(Continued)

FOREIGN PATENT DOCUMENTS

CN    110090012    8/2019
CN    111161884    5/2020
(Continued)

OTHER PUBLICATIONS

Lin Xingfan, "Medical Screening IV—Bayesian probability, odds and probability", Jul. 17, 2012, with English translation thereof, Available at:https://dasanlin888.pixnet.net/blog/post/34469543.
(Continued)

*Primary Examiner* — Rajesh Khattar
*Assistant Examiner* — Steven G. S. Sanghera
(74) *Attorney, Agent, or Firm* — JCIPRNET

(57) ABSTRACT

The disclosure provides a disease classification method and a disease classification device. The disease classification method includes: inputting samples into a first stage model and obtaining a first stage determination result; inputting first samples determined positive by the first stage model into a second stage high specificity model to obtain second samples determined to be positive and third samples determined to be negative and rule in the second samples; inputting fourth samples determined negative by the first stage model into a second stage high sensitivity model to obtain fifth samples determined to be positive and sixth samples determined to be negative and rule out the sixth samples; obtaining a second stage determination result of the second and sixth samples; and inputting the third and fifth samples not ruled in or ruled out into a third stage model and obtaining a third stage determination result of the third and fifth samples.

7 Claims, 5 Drawing Sheets

(56) References Cited

U.S. PATENT DOCUMENTS

| | | | |
|---|---|---|---|
| 10,810,512 B1 * | 10/2020 | Wubbels | ................ G16H 50/20 |
| 2004/0229211 A1 | 11/2004 | Yeung | |
| 2019/0108912 A1 | 4/2019 | Spurlock, III et al. | |
| 2021/0041440 A1 * | 2/2021 | Grimes | ............ G01N 33/57411 |
| 2021/0201190 A1 * | 7/2021 | Edgar | .................... G06N 20/00 |
| 2022/0156932 A1 * | 5/2022 | Fujisawa | ................ G16H 30/40 |

FOREIGN PATENT DOCUMENTS

| | | | | |
|---|---|---|---|---|
| CN | 111436929 | | 7/2020 | |
| CN | 11602150 | | 8/2020 | |
| CN | 109215781 B | * | 11/2021 | ............ G16H 50/20 |
| TW | 200844114 | | 11/2008 | |
| TW | I529652 | | 4/2016 | |
| WO | 2018053604 | | 3/2018 | |
| WO | WO-2019008798 A1 | * | 1/2019 | ............ A61B 5/412 |

OTHER PUBLICATIONS

"Search Report of Europe Counterpart Application", dated May 18, 2021, p. 1-p. 10.

* cited by examiner

DISEASE CLASSIFICATION METHOD AND DISEASE CLASSIFICATION DEVICE

CROSS-REFERENCE TO RELATED APPLICATION

This application claims the priority benefit of Taiwan application serial no. 109131748, filed on Sep. 15, 2020. The entirety of the above-mentioned patent application is hereby incorporated by reference herein and made a part of this specification.

BACKGROUND

Technical Field

The disclosure relates to a disease classification method and disease classification device, and more particularly to a disease classification method and disease classification device which use multiple models to improve the accuracy of disease classification.

Description of Related Art

In medicine, there are many different detection tools available for a disease, and each detection tool has different characteristics. For example, a high sensitivity detection method tends to determine the result to be positive. If the result of this detection method is negative, the reliability will be higher. A high specificity detection method tends to determine the result to be negative. If the result of this detection method is positive, the reliability will be higher.

Usually doctors do not use only a single tool to diagnose whether a patient has a certain disease, but do many tests and then evaluate all the results together. The information required for different tests is also different, such as the patient's basic information, disease history, and values obtained from a certain test, which may be heartbeat, blood pressure, continuous electrocardiography (ECG) values or X-ray pictures, etc.; some of them need to be determined manually by doctors, and some require machines to issue results. Therefore, how to accurately determine the patient's detection results through various models is a goal for people of ordinary skill in the art to work on.

SUMMARY

In view of the above, the disclosure provides a disease classification method and disease classification device which use multiple models to improve the accuracy of disease classification.

The disclosure provides a disease classification method, including: inputting samples into a first stage model and obtaining a first stage determination result; inputting first samples determined to be positive by the first stage model into a second stage high specificity model to obtain second samples determined to be positive and third samples determined to be negative and rule in the second samples; inputting fourth samples determined to be negative by the first stage model into a second stage high sensitivity model to obtain fifth samples determined to be positive and sixth samples determined to be negative and rule out the sixth samples; obtaining a second stage determination result of the second samples and the sixth samples; inputting the third samples and the fifth samples not ruled in or ruled out into a third stage model and obtaining a third stage determination result of the third samples and the fifth samples; calculating a first accuracy according to the first stage determination result and calculating a second accuracy according to the second stage determination result and the third stage determination result; and applying the second stage high specificity model, the second stage high sensitivity model and the third stage model when the second accuracy is greater than the first accuracy.

The disclosure provides a disease classification device including a processor and a memory coupled to the processor. The processor is configured to perform: inputting samples into a first stage model and obtaining a first stage determination result; inputting first samples determined to be positive by the first stage model into a second stage high specificity model to obtain second samples determined to be positive and third samples determined to be negative and rule in the second samples; inputting fourth samples determined to be negative by the first stage model into a second stage high sensitivity model to obtain fifth samples determined to be positive and sixth samples determined to be negative and rule out the sixth samples; obtaining a second stage determination result of the second samples and the sixth samples; inputting the third samples and the fifth samples not ruled in or ruled out into a third stage model and obtaining a third stage determination result of the third samples and the fifth samples; calculating a first accuracy according to the first stage determination result and calculating a second accuracy according to the second stage determination result and the third stage determination result; and applying the second stage high specificity model, the second stage high sensitivity model and the third stage model when the second accuracy is greater than the first accuracy.

Based on the above, the disease classification method and disease classification device of the disclosure use the first stage model to obtain the first stage determination result of multiple samples. The first samples determined to be positive by the first stage model are input to the second stage high specificity model to obtain the second samples determined to be positive and the third samples determined to be negative, and the second samples are ruled in. The fourth samples determined to be negative by the first stage model are input to the second stage high sensitivity model to obtain the fifth samples determined to be positive and the sixth samples determined to be negative, and the sixth samples are ruled out. The third samples and the fifth samples not ruled in or ruled out are input to the third stage model. When the accuracy of the determination result combining the second stage model and the third stage model is greater than the accuracy of the determination result of the first stage model, the second stage high specificity model, the second stage high sensitivity model, and the third stage model are applied to provide the disease prediction result.

DESCRIPTION OF THE EMBODIMENTS

In an embodiment, a disease classification method of the disclosure may include: inputting samples into a first stage model and obtaining a first stage determination result; inputting first samples determined to be positive by the first stage model into a second stage high specificity model to obtain second samples determined to be positive and third samples determined to be negative and rule in the second samples; inputting fourth samples determined to be negative by the first stage model into a second stage high sensitivity model to obtain fifth samples determined to be positive and sixth samples determined to be negative and rule out the sixth samples; obtaining a second stage determination result of the second samples and the sixth samples; inputting the third samples and the fifth samples not ruled in or ruled out into a third stage model and obtaining a third stage determination result of the third samples and the fifth samples; calculating a first accuracy according to the first stage determination result and calculating a second accuracy according to the second stage determination result and the third stage determination result; and applying the second stage high specificity model, the second stage high sensitivity model and the third stage model when the second accuracy is greater than the first accuracy. It is worth noting that ruling in the second samples means that the second samples have a positive detection result in the high specificity model, and ruling out the sixth samples means that the sixth samples have a negative detection result in the high sensitivity model. A specificity of the second stage high specificity model is greater than a first threshold. A sensitivity of the second stage high sensitivity model is greater than a second threshold. A sum of the numbers of the first samples and the fourth samples is equal to the number of the samples. The first stage determination result, the second stage determination result and the third stage determination result include positive and negative results. The first accuracy is calculated based on the first stage determination result and the actual positive or negative attributes of the samples.

In an embodiment, the disease classification device of the disclosure may include a processor and a memory. The memory is coupled to the processor. The memory may store or temporarily store the first stage model, the second stage high specificity model, the second stage high sensitivity model and the third stage model. The processor may execute the steps of the above disease classification method.

Figure 1:
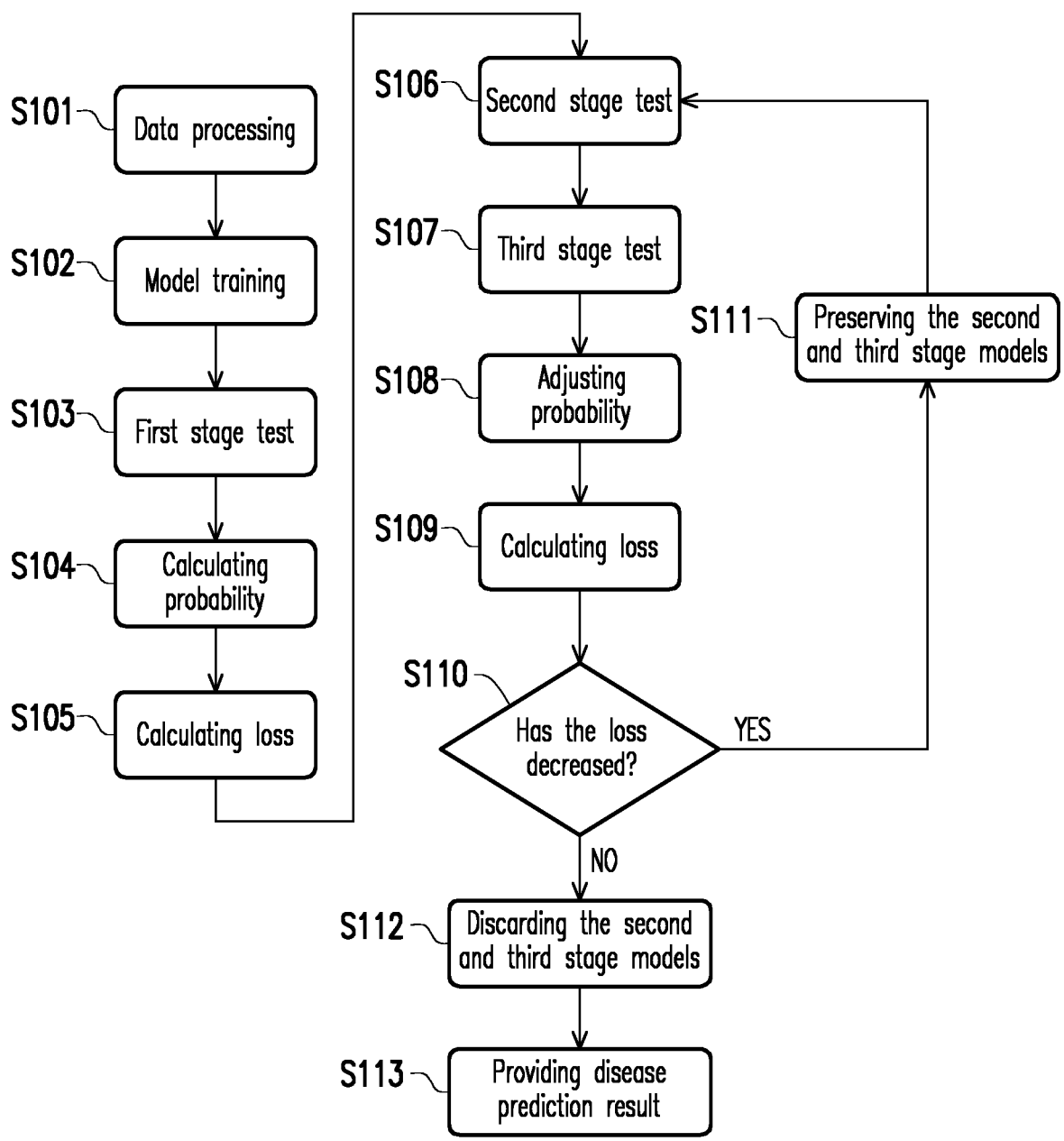
FIG. 1 is a flowchart of a disease classification method according to an embodiment of the disclosure.

FIG. 1 is a flowchart of a disease classification method according to an embodiment of the disclosure.

Please refer to FIG. 1. The disease classification method of an embodiment of the disclosure may first perform data processing (S101) and use the processed data to train a model (S102). After the model training is completed, a first stage test (S103) may be performed, and probability is calculated (S104) and loss is calculated (S105) corresponding to the first stage test. The probability may be a probability which the first stage model outputs for each sample in the first stage test. When the probability of a sample is greater than or equal to a cut point, it means that the determination result of this sample in the first stage model is positive. When the probability of a sample is less than the cut point, it means that the determination result of this sample in the first stage model is negative. The loss may be related to the accuracy of the first stage model. For example, the higher the accuracy of the first stage model is, the smaller the loss is. The accuracy is, for example, the percentage of multiple samples that are correctly determined to be positive or negative by the first stage model.

After calculating the probability and loss of the first stage test, a second stage test may be performed (S106). The second stage test may include the use of the second stage high specificity model and the second stage high sensitivity model to test samples that are determined positive and negative in the first stage test respectively. In the second stage test, samples will be ruled in and ruled out. Samples that are not ruled in or ruled out will enter the third stage test (S107), and the probability will be adjusted (S108). In addition, the loss of the second stage test and the third stage test is calculated (S109), and it is determined whether the loss has decreased compared with the first stage test (S110). If the loss decreases, the second stage model and the third stage model are preserved (S111). If the loss does not decrease, the second stage model and the third stage model are discarded (S112), and the disease prediction result is provided in the end (S113).

Figure 2:
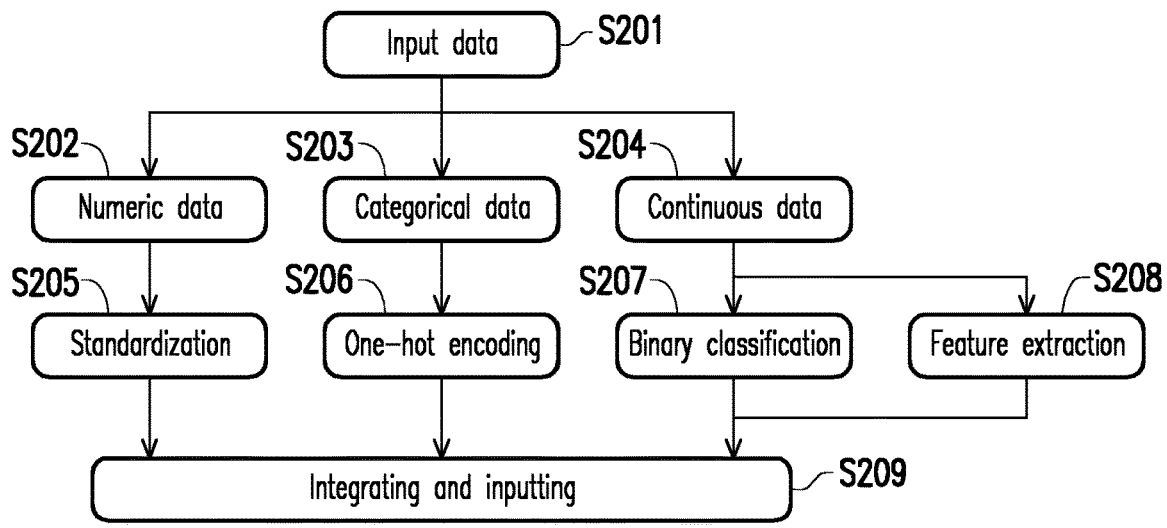
FIG. 2 is a flowchart of data processing according to an embodiment of the disclosure.

FIG. 2 is a flowchart of data processing according to an embodiment of the disclosure.

Please refer to FIG. 2. The data processing and capturing of an embodiment of the disclosure may divide input data (S201) into numeric data (S202), categorical data (S203), and continuous data (S204). The numeric data, the categorical data, and the continuous data may respectively undergo processing of standardization (S205), one-hot encoding (S206), binary classification (S207), and feature extraction (S208) before being integrated and input (S209). Binary classification includes, for example, long short term memory (LSTM) and logistic regression (LR). Feature extraction may include extraction of the maximum, minimum, average, median, etc. of the continuous data.

In an embodiment, in order to build a model, detailed data and diagnosis results of thousands of patients for coronary heart disease diagnosis may be collected. In addition to the basic information and disease history of the patients, an exercise ECG test is also performed to collect additional data, and the data are processed and integrated.

Table 1 is an example of basic clinical data of a patient undergoing a diagnosis of coronary heart disease.

TABLE 1

| Age | 77 |
|---|---|
| Sex | Male |
| Height | 176 |
| Weight | 70.7 |
| Blood type | A |
| Cigarette smoking status | Yes |
| Hyperlipidemia | Yes |
| Hypertension | Yes |
| Diabetes | No |

For numeric data, taking age as an example, set the age of each person as y, the average of all persons as u, and the standard deviation as s, and then convert the age of each person to z, $z=(y-u)/s$. The actual meaning of this standardized value is to show for how many standard deviations the value deviates from the average. This method helps to reduce the impact of unit or full-range differences between different fields. The patient's age in Table 1 is 77 years old.

If the average is 59 years old and the standard deviation is 11, the converted result is (77-59)/11=1.64.

Regarding the categorical data, the blood type is taken as an example. There are 4 types of blood types: A, B, O, and AB. If the blood types are directly converted to codes 1, 2, 3, and 4, the model will mistakenly believe that the distance between type A and type AB is the farthest, but in fact, any two blood types should be equidistant, so the blood type code is converted as shown in the following Table 2.

TABLE 2

| A | 1 | 0 | 0 | 0 |
| B | 0 | 1 | 0 | 0 |
| O | 0 | 0 | 1 | 0 |
| AB | 0 | 0 | 0 | 1 |

Therefore, the blood type will be changed from 1 field to 4 fields. The blood type of the patient in Table 1 is A, and the converted blood type is [1, 0, 0, 0], which is stored as 4 fields.

TABLE 3

| Time | I_ST | I_Slope | II_ST | II_Slope | III_ST | III_Slope |
|---|---|---|---|---|---|---|
| 1 | −0.15 | −0.03 | 0.15 | 0.04 | 0.25 | −0.01 |
| 2 | −0.25 | −1.41 | −0.05 | −0.28 | 0.25 | −0.03 |
| 3 | 0.2 | −2.45 | 0.65 | −0.45 | 0.4 | 1.04 |
| 4 | −0.05 | −0.36 | −0.25 | −0.44 | −0.2 | 0.21 |
| 5 | 0 | −1.19 | 0.5 | −0.49 | −0.3 | 0.78 |
| 6 | −0.3 | −0.73 | −0.9 | −0.26 | −0.55 | −0.96 |
| 7 | −0.1 | 0.44 | −0.85 | 1 | −0.75 | −0.86 |
| 8 | −0.15 | −0.5 | −1.4 | −0.55 | −1.25 | −0.1 |
| 9 | −0.05 | −0.28 | −1.5 | −0.7 | −1.45 | −0.73 |

For continuous data, the method performs statistical feature extraction and uses models to make preliminary predictions. For example, in Table 3, the ST-segment values of the patient's electrocardiography (ECG) at each stage during the exercise ECG test include actually 12 conductive layers (that is, the electrode patch is attached to 12 parts of the patient), and each conductive layer has ST segment time difference and Slope. Table 3 shows the values of the first three conductive layers I_ST, I_Slope, II_ST, II_Slope, III_ST, and III_Slope at each stage.

I_ST is taken as an example, and the average, maximum, minimum, and median of the entire test process are taken as shown in Table 4 below.

TABLE 4

| mean_I_ST | −0.094 |
| max_I_ST | 0.2 |
| min_I_ST | −0.3 |
| med_I_ST | −0.1 |

Continuous data may also be used to build a simple LR model or LSTM model, or a one-dimensional convolutional neural network (CNN) deep learning model, and make predictions to obtain a preliminary probability, which may be used as one of the input fields. After processing, the original continuous data may be discarded, and the extracted features may be used as the subsequent input.

Figure 3:
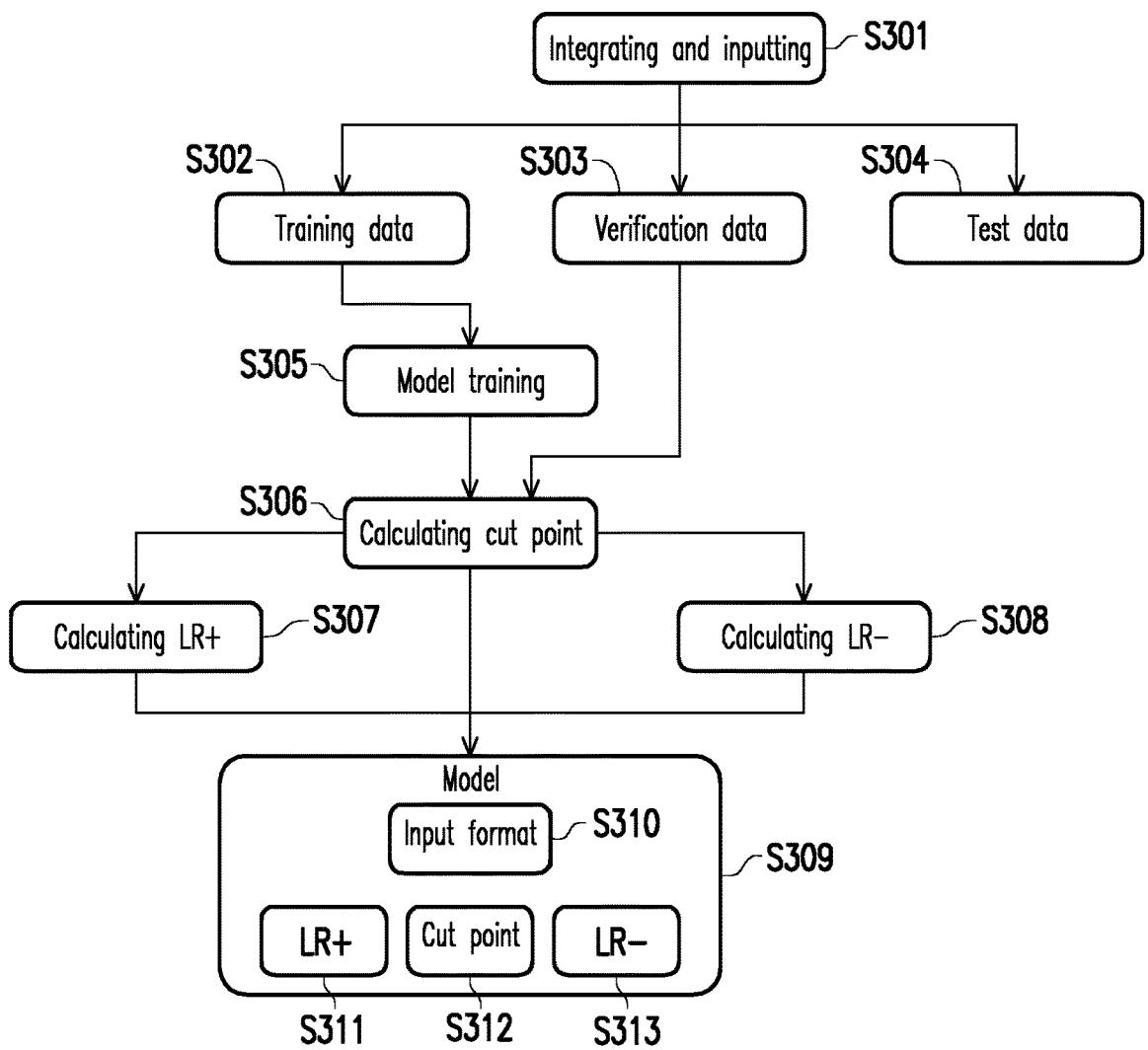
FIG. 3 is a flowchart of model training according to an embodiment of the disclosure.

FIG. 3 is a flowchart of model training according to an embodiment of the disclosure.

Please refer to FIG. 3. In an embodiment, the integrated and input data (S301) may be used as training data (S302), verification data (S303) and test data (S304). The training data may be used to train a model (S305), and the trained model may use the verification data to calculate a cut point (S306), calculate LR+ (S307), and calculate LR− (S308). The final trained model (S309) may include information such as data input format (S310), LR+ (S311), cut point (S312), and LR− (S313).

For example, after integrating the data of each patient, the patient data may be divided into 65% training data, 15% verification data, and 20% test data. The training data is used to train the model. The verification data is used to determine the model cut point and parameters. The test data is later used to evaluate the final effect of the model.

In an embodiment, various machine learning models may be built by using the training data. Different models may also have different inputs according to their needs. The model may predict whether the patient is positive for the disease and output the probability. Table 5 is a list of models.

TABLE 5

| Model | Type |
|---|---|
| Decision Tree | Treebase |
| Random Forest | Treebase Ensemble |
| XGBoost | Treebase Ensemble |
| Gradient Boosting | Treebase Ensemble |
| Extra Tree | Treebase Ensemble |
| AdaBoost | Treebase Ensemble |
| K-Nearest Neighbors | Nearest Neighbors |
| Support Vector Machine (SVM) | Support Vector Machine |
| Logistic Regression | Linear |
| Deep Neural Network (DNN) | Deep Learning |

Regarding the calculation of the cut point, the model output probability must be determined by the cut point to be positive/negative. The cut point is a value between 0 and 1. When the model output probability is greater than or equal to the cut point, it is positive, and when the model output probability is less than the cut point, it is negative. The cut point may be determined by a manually set target. Table 6 below shows commonly used targets in medicine/classification.

TABLE 6

| Target | Description |
|---|---|
| TP | Truly positive and the model determination is also positive |
| FP | Truly negative but the model determination is positive |
| TN | Truly negative and the model determination is also negative |
| FN | Truly positive but the model determination is negative |
| Sensitivity | TP/(TP + FN) |
| Specificity | TN/(TN + FP) |
| PPV | TP/(TP + FP) |
| NPV | TN/(TN + FN) |
| Accuracy | (TP + TN)/(TP + TN + FP + FN) |
| LR+ | Sensitivity/(1 − Specificity) |
| LR− | (1 − Sensitivity)/Specificity |
| LR+/LR− | (TP * TN)/(FP * FN) |

Table 7 below shows the predicted probability of 10 patients obtained by using the Random Forest algorithm model in the validation data. For example, sensitivity and specificity are selected as targets, and weights of 0.4 and 0.6 are given.

TABLE 7

| Actual patient attribute | Random forest algorithm model output probability |
|---|---|
| 0 | 0.6 |
| 0 | 0 |
| 0 | 0.9 |
| 1 | 0.8 |
| 1 | 0.3 |
| 0 | 0.2 |
| 1 | 0 |
| 1 | 0.9 |
| 0 | 0.2 |
| 0 | 0.7 |

The cut point is increased from 0.1 to 0.9 by increasing by 0.1 each time, and the sensitivity and specificity are tested, and the scores are calculated according to the weights. The results are as shown in Table 8 below.

TABLE 8

| | Cut point | | | | | | | | |
|---|---|---|---|---|---|---|---|---|---|
| | 0.1 | 0.2 | 0.3 | 0.4 | 0.5 | 0.6 | 0.7 | 0.8 | 0.9 |
| Sensitivity | 0.75 | 0.75 | 0.75 | 0.50 | 0.50 | 0.50 | 0.50 | 0.50 | 0.25 |
| Specificity | 0.17 | 0.17 | 0.50 | 0.50 | 0.50 | 0.50 | 0.67 | 0.83 | 0.83 |
| Score | 0.4 | 0.4 | 0.6 | 0.5 | 0.5 | 0.5 | 0.6 | 0.7 | 0.6 |

As shown in Table 8, the score is highest when the cut point is 0.8. Therefore, the cut point of 0.8 is chosen in the end, and it is recorded that the random forest algorithm model has the cut point of 0.8, LR+ of 3, and LR− of 0.6.

Figure 4:
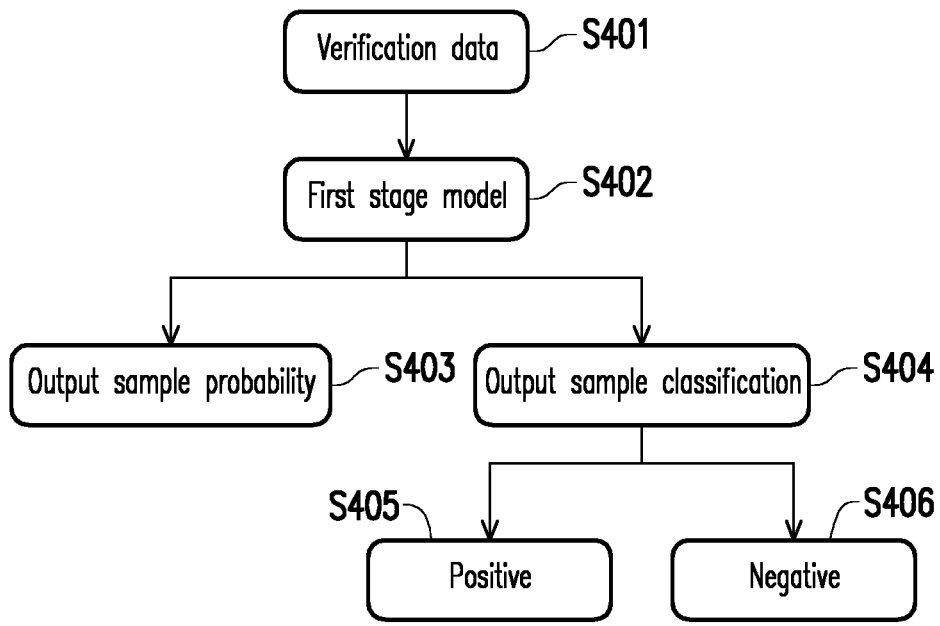
FIG. 4 is a flowchart of the first stage test according to an embodiment of the disclosure.

FIG. 4 is a flowchart of the first stage test according to an embodiment of the disclosure.

Please refer to FIG. 4. The verification data (S401) is input to the first stage model (S402) for the output sample probability (S403) and the output sample classification (S404). The output sample classification may include positive samples (S405) and negative samples (S406).

For example, in the first stage model test, the random forest algorithm model is used as the first stage model. Table 9 below shows two samples in the verification data (i.e., samples with the cut point of 0.8). In addition to the determination result, the probability output by the first stage model (i.e., the pre-test probability) will also be recorded.

TABLE 9

| Sample | Random forest algorithm model prediction probability | Determination result |
|---|---|---|
| 1 | 0.6 | 0 (Negative) |
| 2 | 0.9 | 1 (Positive) |

Before entering the second and third stages, the accuracy of the current first stage model may be calculated. If the accuracy of the second and third stages is not improved, the second and third stage models are discarded. Table 10 records the results of the verification data in the first stage, and uses the measurement value of the accuracy corresponding to the loss (LOSS) in Table 6. The higher the accuracy is, the better it is.

TABLE 10

| Actual patient attribute | First stage model determination result | Random forest algorithm model output probability |
|---|---|---|
| 0 | 0 | 0.6 |
| 0 | 0 | 0 |
| 0 | 1 | 0.9 |
| 1 | 1 | 0.8 |
| 1 | 0 | 0.3 |
| 0 | 0 | 0.2 |
| 1 | 0 | 0 |
| 1 | 1 | 0.9 |
| 0 | 0 | 0.2 |
| 0 | 0 | 0.7 |

It may be seen from Table 10 that the accuracy is 70%. In other words, the actual patient attributes of 7 pieces out of 10 pieces of data are the same as the first stage determination result.

Figure 5:
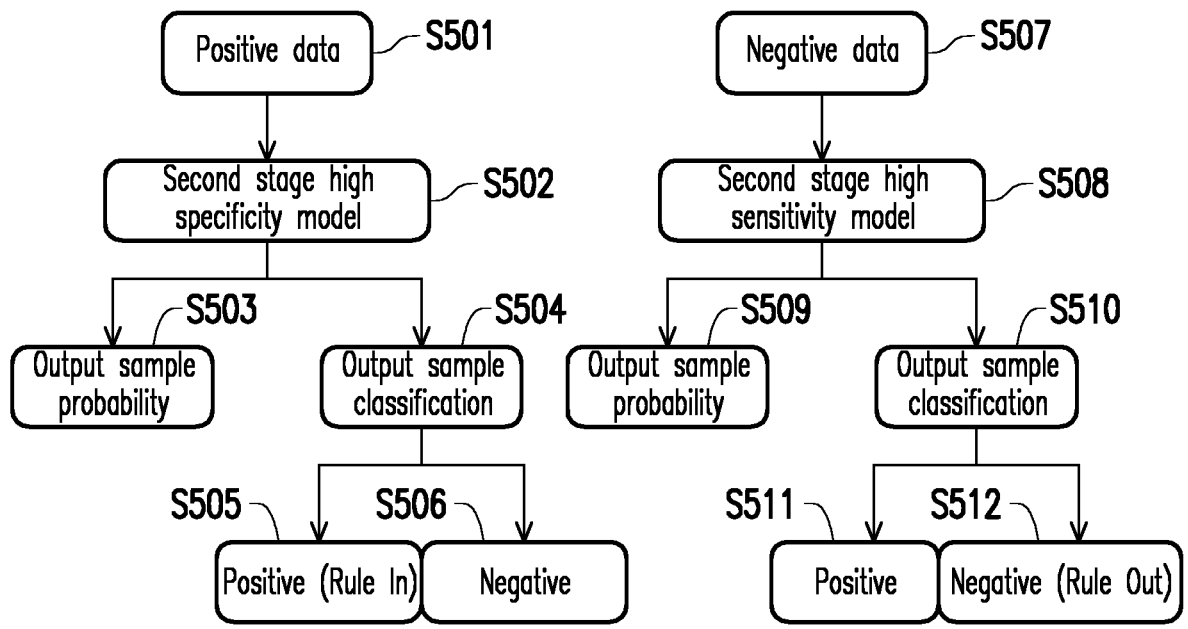
FIG. 5 is a flowchart of the second stage ruling in and ruling out according to an embodiment of the disclosure.

FIG. 5 is a flowchart of the second stage ruling in and ruling out according to an embodiment of the disclosure.

Please refer to FIG. 5. The positive data determined in the first stage (S501) may be input into the second stage high specificity model (S502) to generate the output sample probability (S503) and the output sample classification (S504). The output sample classification may include positive samples (S505) and negative samples (S506). The positive samples output by the high specificity model may be ruled in (Rule In). The negative data determined in the first stage (S507) may be input into the second stage high sensitivity model (S508) to generate the output sample probability (S509) and the output sample classification (S510). The output sample classification may include positive samples (S511) and negative samples (S512). The negative samples output by the high sensitivity model may be ruled out (Rule Out). That is to say, in the second stage, the positive data is sent to the high specificity model (i.e., the model that tends to determine the sample to be negative), and the second stage model also has the cut point and LR+ and LR−. The output probability of the second stage model may be used to determine the second stage determination result. If the second stage high specificity model also determines the sample to be positive, there is a high probability that the positive result is true (i.e., ruled in). Similarly, in the second stage, the negative data is sent to the high sensitivity model (i.e., the model that tends to determine the sample to be positive). If the second stage high sensitivity model also determines the sample to be negative, there is a high probability that the negative result is true (i.e., ruled out).

Figure 6:
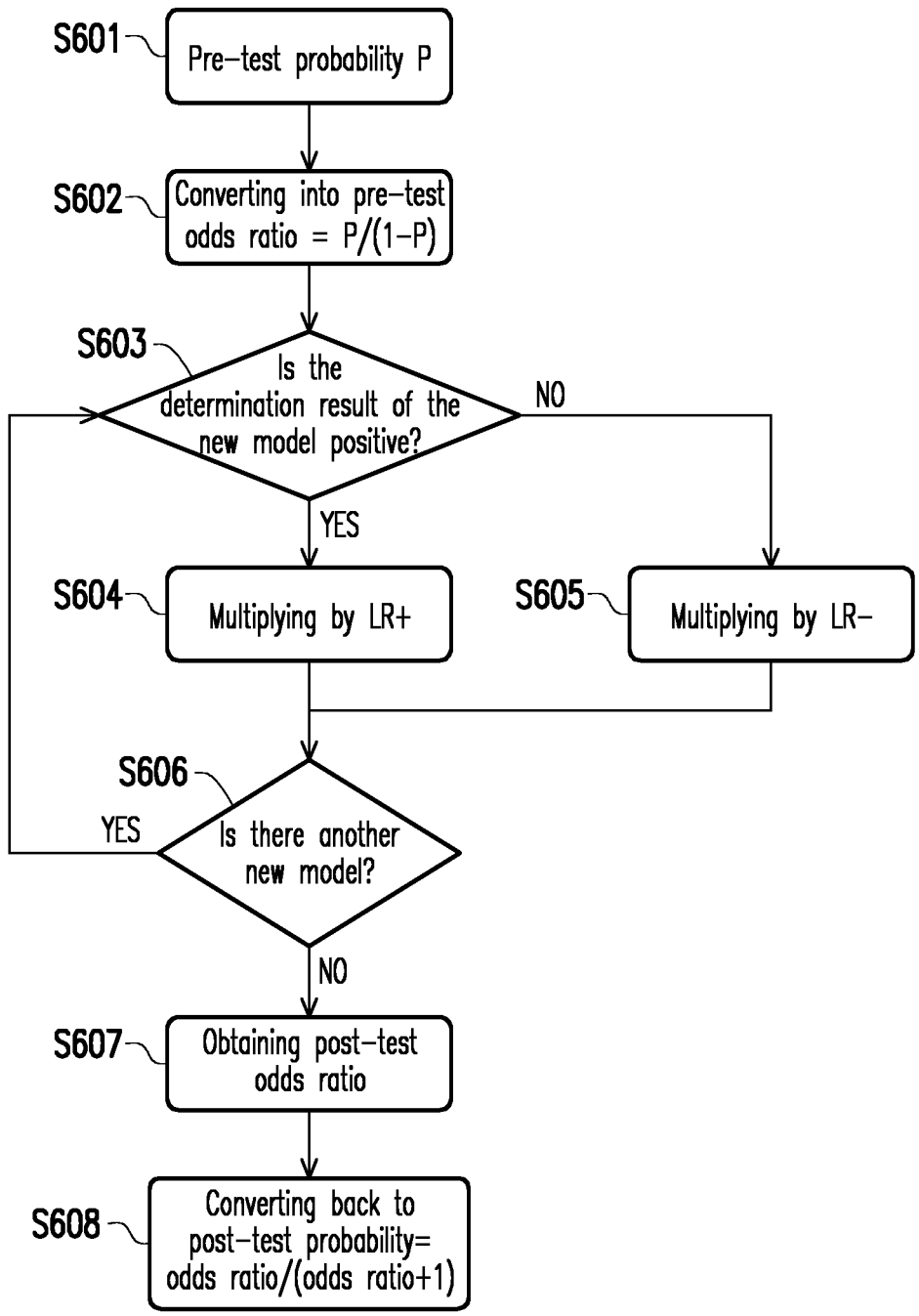
FIG. 6 is a flowchart of calculating the adjusted probability of the second stage model or the adjusted probability of the third stage model according to an embodiment of the disclosure.

In an embodiment, the output probability of the first stage may be adjusted according to the LR+ and LR− of the second stage model, instead of directly using the second stage model output probability as the prediction probability. FIG. 6 is a flowchart of calculating the adjusted probability of the second stage model or the adjusted probability of the third stage model according to an embodiment of the disclosure. Please refer to FIG. 6. The output sample probability of the first stage model may be used as the pre-test probability P of the second stage model and the third stage model (S601). The pre-test probability P may be converted into the pre-test odds ratio=P/(1−P) (S602). It may be determined whether the new model (such as the second stage model or the third stage model) determines the sample to be positive (S603). If the determination of the new model is positive, the pre-test odds ratio is multiplied by the LR+ of the new model (S604). If the determination of the new model is negative, the pre-test odds ratio is multiplied by the LR− of the new model (S605). Next, it is determined whether there is another new model (S606). If there is another new model, such as a third stage model, it is returned to step S603 to continue to determine whether the determination of the third stage model is positive. If there is not any new model, a post-test odds ratio is obtained by multiplying the pre-test odds ratio by LR+ or LR− (S607), and the post-test odds ratio is converted back to the post-test probability=the post-test odds ratio/(the post-test odds ratio+1).

For example, suppose the cut point of the second stage high sensitivity model is 0.3, LR+=1.5, and LR−=0.3. The cut point of the second stage high specificity model is 0.8, LR+=3, and LR−=0.6. Here, the output probability of the second stage is omitted, and only the determination result of the second stage is listed. The following is an example of adjusting the output probability of the second stage.

[Example of Adjusting the Output Probability of the Second Stage]

Step 1: The first stage output probability is 0.6 (or called the first output probability).

Step 2: The first stage odds ratio=0.6/0.4=1.5 (or called the first odds ratio).

Step 3: The sample determined to be negative in the first stage is sent to the second stage high sensitivity model and determined to be positive. The LR+ of the high sensitivity model is 1.5. The second stage odds ratio=1.5*1.5=2.25 (or called the second odds ratio).

Step 4: The adjusted output probability of the second stage=2.25/(2.25+1)=0.69 (or called the second output probability).

Table 11 is an example of the adjusted output probability of the second stage (i.e., the post-test probability).

TABLE 11

| Actual patient attribute | First stage determination result | First stage output probability | Second stage determination result | Second stage adjusted probability |
|---|---|---|---|---|
| 0 | 0 | 0.6 | 1 | 0.69 |
| 0 | 0 | 0 | 0 (Rule Out) | 0 |
| 0 | 1 | 0.9 | 1 (Rule In) | 0.96 |
| 1 | 1 | 0.8 | 1 (Rule In) | 0.92 |
| 1 | 0 | 0.3 | 1 | 0.39 |
| 0 | 0 | 0.2 | 0 (Rule Out) | 0.07 |
| 1 | 0 | 0 | 1 | 0 |
| 1 | 1 | 0.9 | 1 (Rule In) | 0.96 |
| 0 | 0 | 0.2 | 0 (Rule Out) | 0.07 |
| 0 | 0 | 0.7 | 1 | 0.78 |

Figure 7:
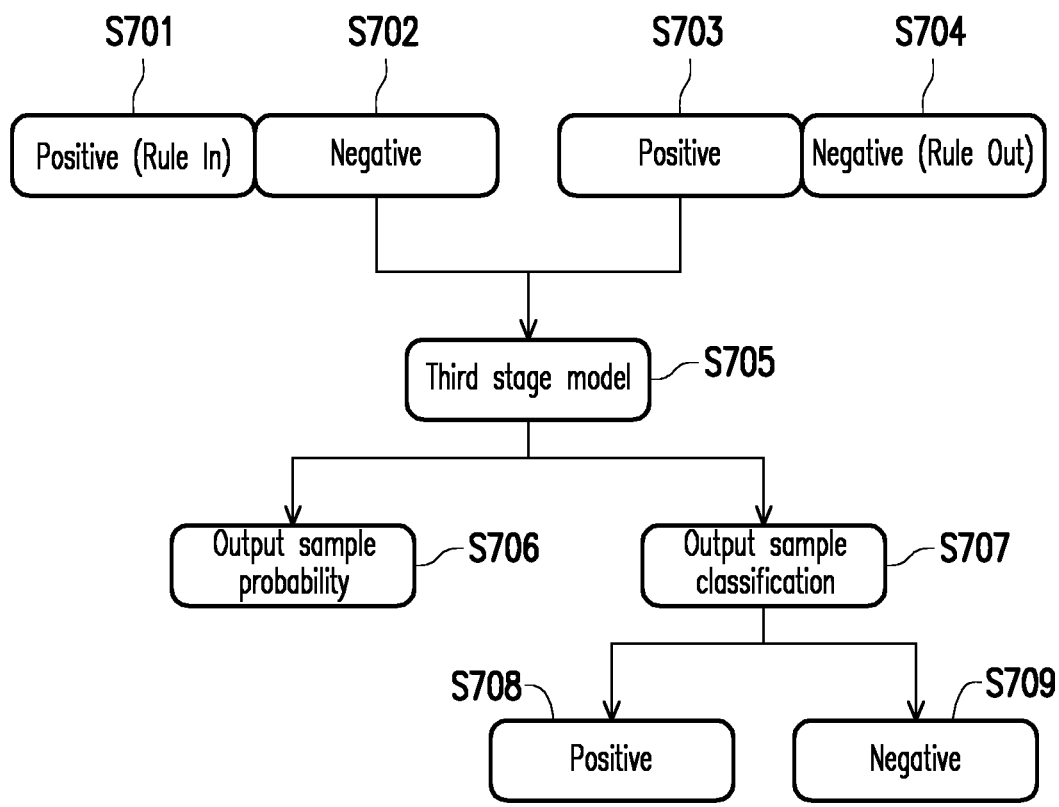
FIG. 7 is a flowchart of the third stage test according to an embodiment of the disclosure.

FIG. 7 is a flowchart of the third stage test according to an embodiment of the disclosure.

Please refer to FIG. 7. The output sample classification of the second stage model may include positive samples (S701) output by the second stage high specificity model and ruled in (Rule In) and negative samples output by the second stage high specificity model (S702). The output sample classification of the second stage model may also include positive samples output by the second stage high sensitivity model (S703) and negative samples output by the second stage high sensitivity model and ruled out (Rule Out) (S704). Only the negative samples output by the second stage high specificity model and the positive samples output by the second stage high sensitivity model that have not been ruled in or ruled out in the second stage are input into the third stage model (S705) to generate the output sample probability (S706) and the output sample classification (S707). The output sample classification may include positive samples (S708) and negative samples (S709).

For example, suppose that the cut point of the third stage model is 0.5, LR+=2, and LR−=0.5. The following is an example of adjusting the output probability of the third stage.

[Example of Adjusting the Output Probability of the Third Stage]

Step 1: The first stage output probability is 0.6.

Step 2: The first stage odds ratio=0.6/0.4=1.5.

Step 3: The sample determined to be negative in the first stage is sent to the second stage high sensitivity model and determined to be positive. The LR+ of the second stage high sensitivity model is 1.5. The sample is determined to be negative by the third stage model, and the LR− of the third stage model is 0.5. The third stage odds ratio=1.5*1.5*0.5=1.125 (or called the third odds ratio).

Step 4: The adjusted output probability of the third stage=1.125/(1.125+1)=0.53 (or called the third output probability).

Table 12 is an example of the adjusted output probability of the third stage (i.e., the post-test probability).

TABLE 12

| Actual attribute | First stage result | First stage probability | Second stage result | Second stage adjusted probability | Third stage result | Third stage adjusted probability |
|---|---|---|---|---|---|---|
| 0 | 0 | 0.6 | 1 | 0.69 | 0 | 0.53 |
| 1 | 0 | 0.3 | 1 | 0.39 | 1 | 0.56 |
| 1 | 0 | 0 | 1 | 0 | 0 | 0 |
| 0 | 0 | 0.7 | 1 | 0.78 | 0 | 0.64 |

According to the information in Table 12 and Table 11 of being ruled in or ruled out in the second stage determination result, the accuracy of the determination result combining the second stage model and the third stage model may be obtained as 80%. Since the accuracy (for example, 80%) of the determination result combining the second stage model and the third stage model is greater than the accuracy (for example, 70%) of the determination result of the first stage model, the second stage model and the third stage model may be applied for more data verification. If the accuracy of the determination result combining the second stage model and the third stage model is less than or equal to the accuracy of the determination result of the first stage model, the second stage model and the third stage model are discarded, and other models may be found as new second stage model and third stage model.

In an embodiment, a model may also set a positive threshold and a negative threshold. For example, the post-test probability of a sample determined to be positive by the model must be greater than the positive threshold before being determined to be positive. The post-test probability of a sample determined to be negative by the model must be less than the negative threshold before being determined to be negative.

In summary, the disease classification method and disease classification device of the disclosure use the first stage model to obtain the first stage determination result of multiple samples. The first samples determined to be positive by the first stage model are input to the second stage high specificity model to obtain the second samples determined to be positive and the third samples determined to be negative, and the second samples are ruled in. The fourth samples determined to be negative by the first stage model are input to the second stage high sensitivity model to obtain the fifth samples determined to be positive and the sixth samples determined to be negative, and the sixth samples are ruled out. The third samples and the fifth samples not ruled in or ruled out are input to the third stage model. When the accuracy of the determination result combining the second stage model and the third stage model is greater than the accuracy of the determination result of the first stage model, the second stage high specificity model, the second stage high sensitivity model, and the third stage model are applied to provide the disease prediction result.

Although the disclosure has been described with reference to the above embodiments, it will be apparent to one of ordinary skill in the art that modifications to the described embodiments may be made without departing from the spirit of the disclosure. Accordingly, the scope of the disclosure will be defined by the attached claims and their equivalents and not by the above detailed descriptions.

What is claimed is:

1. A disease classification method, adapted to a disease classification device having a processor, comprising:
inputting, by the processor, samples into a first stage model which is a machine learning model trained by using a data set of basic clinical data and diagnosis results of a plurality of patients for diseases to be classified, to obtain a first stage determination result comprising first samples determined to be positive and fourth samples determined to be negative, wherein a sum of numbers of the first samples and the fourth samples is equal to a number of the samples;
obtaining, by the processor, second samples determined to be positive and third samples determined to be negative via inputting first samples determined to be positive by the first stage model into a second stage specificity model which is a machine learning model trained by using the data set and having a specificity greater than a first threshold and ruling in, by the processor, the second samples;
obtaining, by the processor, fifth samples determined to be positive and sixth samples determined to be negative via inputting the fourth samples determined to be negative by the first stage model into a second stage sensitivity model which is a machine learning model trained by using the data set and having a sensitivity greater than a second threshold and ruling out, by the processor, the sixth samples;
determining, by the processor, a second stage determination result of the second samples and the sixth samples;
inputting, by the processor, the third samples and the fifth samples not ruled in or ruled out into a third stage model which is a machine learning model trained by using the data set and having a LR+, a LR− and a cut point between the LR+, the LR− and the cut point of the second stage specificity model and the second stage sensitivity model to determine a third stage determination result of the third samples and the fifth samples;
determining, by the processor, a first accuracy according to the first stage determination result and actual positive or negative attributes of the samples, and determining, by the processor, a second accuracy according to the second stage determination result and the third stage determination result;
in response to determining that the second accuracy is greater than the first accuracy, providing disease prediction results obtained by applying the second stage specificity model, the second stage sensitivity model and the third stage model; and
in response to determining that the second accuracy is not greater than the first accuracy, discarding the disease prediction results obtained by applying the second stage specificity model, the second stage sensitivity model and the third stage model.

2. The disease classification method according to claim 1, further comprising:
determining a second output probability of the second stage specificity model or the second stage sensitivity model according to a first output probability of the first stage model and LR+ or LR− of the second stage specificity model or the second stage sensitivity model, and obtaining the second stage determination result according to the second output probability.

3. The disease classification method according to claim 2, further comprising:
determining a first odds ratio according to a first output probability of a seventh sample among the samples in the first stage model, wherein
a second odds ratio is obtained by multiplying the first odds ratio by the LR+ of the second stage specificity model or the second stage sensitivity model when the seventh sample is determined to be positive by the second stage specificity model or the second stage sensitivity model,
the second odds ratio is obtained by multiplying the first odds ratio by the LR− of the second stage specificity model or the second stage sensitivity model when the seventh sample is determined to be negative by the second stage specificity model or the second stage sensitivity model, and
a second output probability is determined according to the second odds ratio.

4. The disease classification method according to claim 3, wherein the first odds ratio=the first output probability/(1−the first output probability), and the second output probability=the second odds ratio/(the second odds ratio+1).

5. The disease classification method according to claim 3, wherein the seventh sample is not ruled out or ruled in by the second stage specificity model or the second stage sensitivity model,
a third odds ratio is obtained by multiplying the second odds ratio by LR+ of the third stage model when the seventh sample is determined to be positive by the third stage model,
the third odds ratio is obtained by multiplying the second odds ratio by LR− of the third stage model when the seventh sample is determined to be negative by the third stage model, and
a third output probability is calculated according to the third odds ratio.

6. The disease classification method according to claim 5, wherein the third output probability=the third odds ratio/(the third odds ratio+1).

7. A disease classification device, comprising:
a processor; and
a memory coupled to the processor,
wherein the processor is configured to perform:
inputting samples into a first stage model which is a machine learning model trained by using a data set of basic clinical data and diagnosis results of a plurality of patients for diseases to be classified, to obtain a first stage determination result comprising first samples determined to be positive and fourth samples determined to be negative, wherein a sum of numbers of the first samples and the fourth samples is equal to a number of the samples;
obtaining second samples determined to be positive and third samples determined to be negative via inputting first samples determined to be positive by the first stage model into a second stage specificity model which is a machine learning model trained by using the data set and having a specificity greater than a first threshold and ruling in the second samples;

obtaining fifth samples determined to be positive and sixth samples determined to be negative via inputting the fourth samples determined to be negative by the first stage model into a second stage sensitivity model which is a machine learning model trained by using the data set and having a sensitivity greater than a second threshold and ruling out the sixth samples;

determining a second stage determination result of the second samples and the sixth samples;

inputting the third samples and the fifth samples not ruled in or ruled out into a third stage model which is a machine learning model trained by using the data set and having a LR+, a LR− and a cut point between the LR+, the LR− and the cut point of the second stage specificity model to determine a third stage determination result of the third samples and the fifth samples;

determining a first accuracy according to the first stage determination result and actual positive or negative attributes of the samples, and determining a second accuracy according to the second stage determination result and the third stage determination result;

in response to determining that the second accuracy is greater than the first accuracy, providing disease prediction results obtained by applying the second stage specificity model, the second stage sensitivity model and the third stage model; and in response to determining that the second accuracy is not greater than the first accuracy, discarding the disease prediction results obtained by applying the second stage specificity model, the second stage sensitivity model and the third stage model.

* * * * *